United States Patent
Freitag

(10) Patent No.: US 11,799,172 B2
(45) Date of Patent: Oct. 24, 2023

(54) DUAL SEPARATOR DESIGN FOR MEDICAL IMPLANTABLE ELECTROCHEMICAL CELLS

(71) Applicant: Greatbatch Ltd., Clarence, NY (US)

(72) Inventor: Gary Freitag, East Aurora, NY (US)

(73) Assignee: Greatbatch Ltd., Clarence, NY (US)

( * ) Notice: Subject to any disclaimer, the term of this patent is extended or adjusted under 35 U.S.C. 154(b) by 56 days.

(21) Appl. No.: 17/505,712

(22) Filed: Oct. 20, 2021

(65) Prior Publication Data

US 2022/0131234 A1 Apr. 28, 2022

Related U.S. Application Data

(60) Provisional application No. 63/104,561, filed on Oct. 23, 2020.

(51) Int. Cl.
| | |
|---|---|
| *H01M 50/46* | (2021.01) |
| *H01M 50/103* | (2021.01) |
| *H01M 50/188* | (2021.01) |
| *H01M 50/147* | (2021.01) |
| *H01M 50/466* | (2021.01) |
| *H01M 4/54* | (2006.01) |
| *H01M 4/583* | (2010.01) |
| *H01M 4/587* | (2010.01) |
| *H01M 10/0525* | (2010.01) |
| *A61N 1/378* | (2006.01) |

(52) U.S. Cl.
CPC .............. *H01M 50/46* (2021.01); *H01M 4/54* (2013.01); *H01M 4/587* (2013.01); *H01M 4/5835* (2013.01); *H01M 10/0525* (2013.01); *H01M 50/103* (2021.01); *H01M 50/147* (2021.01); *H01M 50/188* (2021.01); *H01M 50/466* (2021.01); *A61N 1/378* (2013.01)

(58) Field of Classification Search
CPC .. H01M 50/46; H01M 50/103; H01M 50/188; H01M 50/147; H01M 50/466; H01M 4/54; H01M 4/5835; H01M 4/587; H01M 10/0525; A61N 1/378
See application file for complete search history.

(56) References Cited

U.S. PATENT DOCUMENTS

| | | | |
|---|---|---|---|
| 4,310,609 | A | 1/1982 | Liang et al. |
| 4,391,729 | A | 7/1983 | Liang et al. |
| 5,250,373 | A | 10/1993 | Muffoletto et al. |
| 5,415,959 | A | 5/1995 | Pyszczek et al. |

(Continued)

*Primary Examiner* — Brian R Ohara
*Assistant Examiner* — Emily Elizabeth Freeman
(74) *Attorney, Agent, or Firm* — Michael F. Scalise

(57) ABSTRACT

An electrochemical cell comprises a casing having an open-ended container closed by a lid. An anode and cathode are housed inside the casing. The cathode housed inside a primary separator envelope is electrically connected to a positive polarity terminal pin electrically isolated from the casing by a glass-to- The anode is electrically connected to the casing metal seal.
serving as a negative terminal. The primary separator enveloping the cathode is contained in a secondary separator comprising an open-ended bag-shaped member extending to an open annular edge. The open annular edge of the secondary separator resides between the cathode electrically connected to the terminal pin and the anode electrically connected to the casing. An electrolyte provided in the casing activates the anode and cathode.

21 Claims, 3 Drawing Sheets

(56) References Cited

U.S. PATENT DOCUMENTS

| | | | |
|---|---|---|---|
| 5,472,810 A | 12/1995 | Takeuchi et al. | |
| 5,516,340 A | 5/1996 | Takeuchi et al. | |
| 5,631,102 A | 5/1997 | Spillman et al. | |
| 5,750,286 A | 5/1998 | Paulot et al. | |
| 5,902,696 A | 5/1999 | Smesko et al. | |
| 6,475,666 B1 | 11/2002 | Takeuchi | |
| 6,551,747 B1 | 4/2003 | Gan | |
| 6,593,028 B1 | 7/2003 | McCormick | |
| 7,875,379 B2 | 1/2011 | Moceri et al. | |
| 7,958,922 B2 | 6/2011 | Seitz et al. | |
| 9,978,528 B2 | 5/2018 | Hahl et al. | |
| 2017/0148576 A1* | 5/2017 | Hahl | H01G 9/0425 |

* cited by examiner

DUAL SEPARATOR DESIGN FOR MEDICAL IMPLANTABLE ELECTROCHEMICAL CELLS

CROSS-REFERENCE TO RELATED APPLICATION

This application claims priority to U.S. provisional application Ser. No. 63/104,561, filed on Oct. 23, 2020.

FIELD OF THE INVENTION

The present invention relates to the art of electrochemical cells. More particularly, the present electrochemical cell has a new separator system for preventing direct physical contact between both the anode and cathode active materials and their electrical connections to the positive and negative cell terminals.

BACKGROUND OF THE INVENTION

A prismatic electrode configuration is a commonly used design for an electrochemical cell. In a case-negative prismatic electrochemical cell, a cathode is centered between two spaced-apart anode plates. The cathode is electrically connected to a terminal pin that is electrically isolated from the cell casing by a glass-to-metal seal and serves as the positive terminal for the cell. The anode plates are electrically connected to the casing, which serves as the negative terminal for the cell.

To prevent the opposite polarity electrodes from physically contacting each other, the anode plates and the intermediate cathode are isolated using a separator material that prevents physical contact but allows for ion transfer. Additional insulators are also needed to electrically isolate other portions of opposite polarity within the casing, for example, the opposite polarity electrode leads and the casing. Moreover, in cells where reliability is critical, two layers of microporous separator material are used. This redundant separator system helps prevent any defect in one of the microporous layers from being the site of a short-circuit. The combination of multiple separator layers and other insulators within the casing take up a greater percentage of volume as the size of the casing is reduced.

Thus, there is a need for an improved separator and insulator system that adequately prevents physical contact between the opposite polarity electrode, but that takes up less space inside the casing than is presently needed for a conventional separator and insulator system.

SUMMARY OF THE INVENTION

The separator system of the present invention employs a novel approach where the intermediate cathode in a case-negative cell design is first housed in a separator envelope made of two layers of microporous woven or non-woven polymeric material, preferably a fluoro-polymeric material. The first separator envelope is heat sealed at a seam to completely enclose the cathode. To provide a degree of redundancy that is important in electrochemical cells that are intended to power devices where failure is critical, such as cells that are intended to power implantable medical devices, for example a cardiac pacemaker or a cardiac defibrillator, the cathode/first separator envelope subassembly is housed inside a second separator bag.

However, unlike the first separator envelope that completely encloses the cathode, the second separator bag is a free-standing open-ended bag. The upper open end of the free-standing bag extends upwardly toward the case lid so that its upper edge is spaced a relatively short distance from the lid. That way, the free-standing separator bag not only provides the desired redundancy to prevent the anode and the cathode from physical contact with each other, but the upper portion of the second separator bag acts as a physical barrier between the positive polarity terminal pin electrically connected to the cathode current collector and the negative polarity anode tabs extending from the anode current collectors electrically connected to the casing wall. As electrochemical cells become increasingly smaller, the distance between these opposite polarity non-active components becomes smaller with the real possibility for direct physical contact. Such contact is prevented by the free-standing open-ended second separator bag.

These and other aspects of the present invention will become increasingly more apparent to those skilled in the art by reference to the following detailed description and to the appended drawings.

DETAILED DESCRIPTION OF THE PREFERRED EMBODIMENTS

With respect to the annular edge of the secondary separator or the open-ended annular edge of the secondary separator, the term "annular" is defined as of, relating to, or forming a ring.

Figure 1:
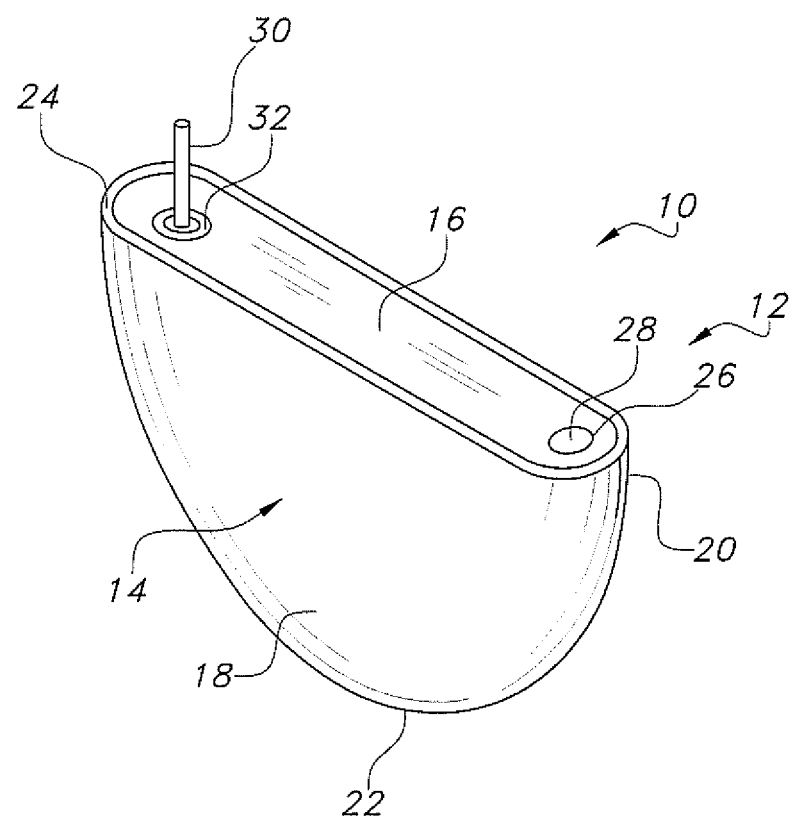
FIG. 1 is a perspective view of an exemplary prismatic cell 10 according to the present invention.
Figure 2:
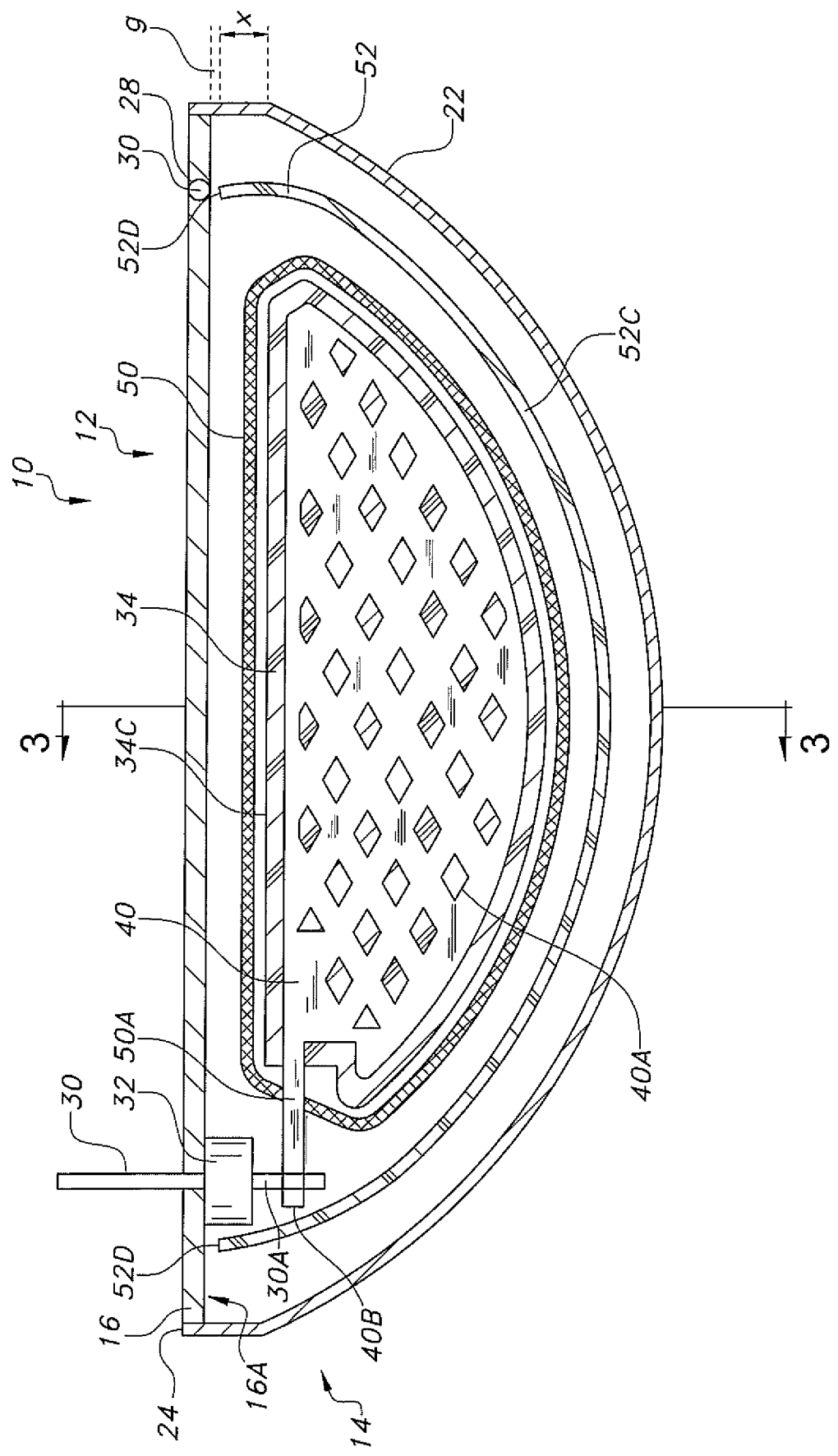
FIG. 2 is an enlarged cross-sectional side elevational view of the prismatic electrochemical cell 10 shown in FIG. 1.
Figure 3:
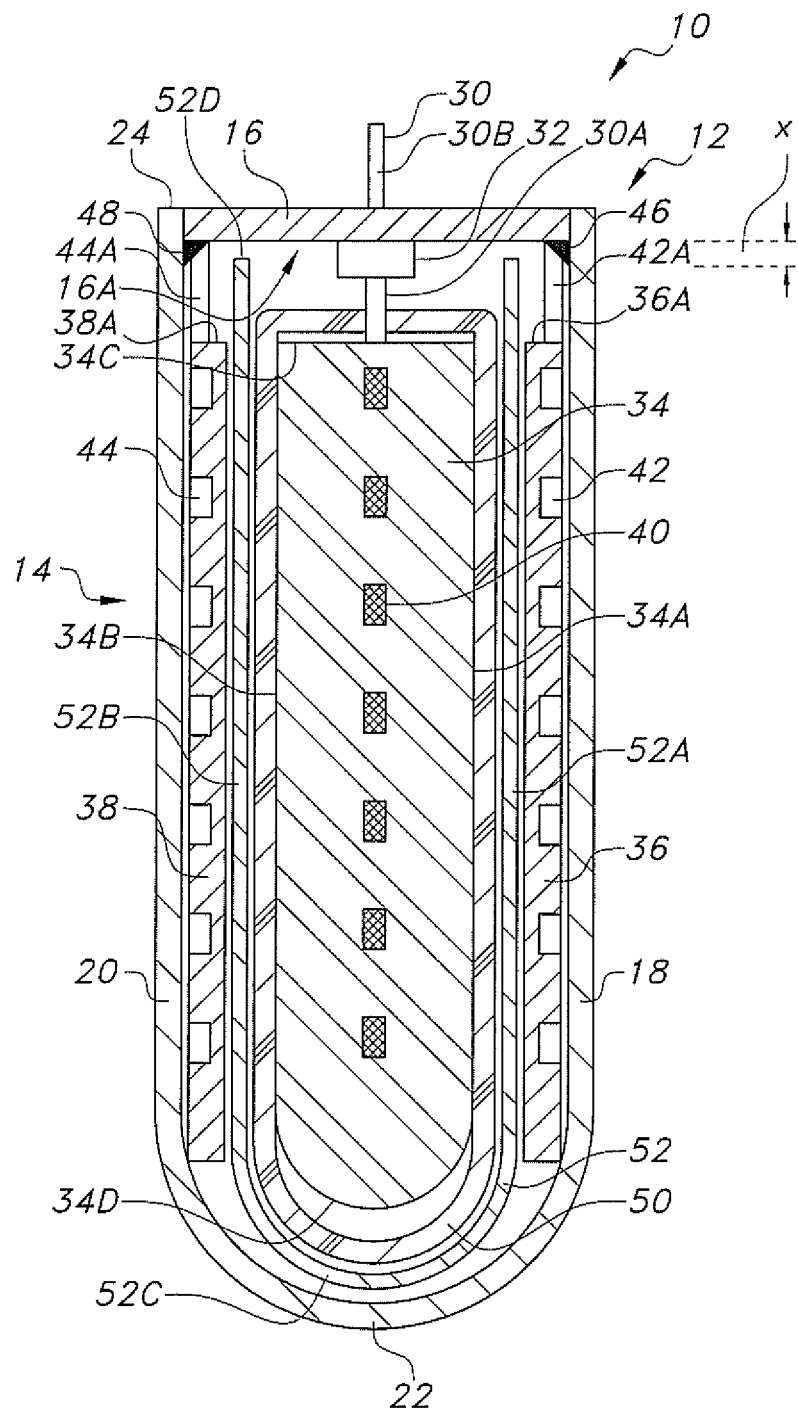
FIG. 3 is a cross-sectional view taken along line 3-3 of FIG. 2.

Turning now to the drawings, a perspective view of an exemplary prismatic-type electrochemical cell 10 according to the present invention is shown in FIGS. 1 to 3. Although the electrochemical cell 10 is described and illustrated with respect to an electrode assembly of a primary chemistry housed inside a prismatic casing, those skilled in the art will recognize that the present separator configuration is also adaptable to electrochemical cells of a secondary chemistry and, in addition to a prismatic design, to many different types of cell designs including cylindrical and button-type cells.

The exemplary prismatic electrochemical cell 10 has a casing 12 comprising an open-ended container 14 closed by a lid 16. The open-ended container 14 has spaced-apart front and back sidewalls 18 and 20 joined to an end wall 22 having a generally radius curved shape meeting the sidewalls 18, 20. The sidewalls 18, 20 and the intermediate curved end wall 22 together form a peripheral edge 24 surrounding an open end of the casing container 14. As will be described in detail hereinafter, after an electrode assembly is housed inside the container 14, the lid 16 is welded to its open end at the peripheral edge 24 to thereby provide the casing 12.

The lid 16 has an opening 26 that is used for filling an electrolyte (not shown) into the casing 12 to activate the electrode assembly. In its fully assembled condition, a closure means 28 is hermetically secured in the fill opening 26 to seal the casing 12.

A cathode terminal pin 30, which is electrically isolated from the casing 12 by a glass-to-metal seal 32, comprises a terminal pin proximal portion 30A residing inside the casing 12, and a terminal pin distal portion 30B extending outside the casing. The terminal pin distal portion 30B is configured for electrically connection to a load that will be powered by the electrochemical cell 10.

FIGS. 2 and 3 are cross-sectional views of an exemplary prismatic electrode assembly housed inside the casing 12. In the illustrated prismatic design, a central cathode 34 is flanked on both of its major sides by anode plates 36 and 38. The cathode 34 is a solid body in the form of a cathode active mixture pressed or calendared against a cathode current collector 40. The cathode 34 has opposing major sidewalls 34A and 34B shaped to conform to the front and back sidewalls 18 and 20 of the casing 12. The cathode sidewalls 34A and 34B extend to and meet a generally planar top wall 34C and a curved bottom wall 34D. The top wall 34C resides adjacent to the lid 16 while the bottom wall 34D is curved to match the curved end wall 22 of the casing container 14. The cathode side walls 34A and 34B are contoured to match the shape of the spaced apart front and back walls 18 and 20 of the casing 12.

The cathode current collector 40 comprises an apertured grid 40A connected to a continuous and outwardly extending connection tab 40B in the form of a land. FIG. 2 shows the proximal portion 30A of the terminal pin 30 electrically connected to a distal portion of the current collector connection tab 40B, however, the pin 30 can be electrically connected to the connection tab 40B at any location along its full extent. This construction of a terminal pin electrically connected to the connection tab of a cathode current collector is more thoroughly described in U.S. Pat. No. 5,750,286 to Paulot et al., which is assigned to the assignee of the present invention and incorporated herein by reference.

FIGS. 2 and 3 further show that the anode plates 36 and 38 are pressed bonded to respective anode current collectors 42 and 44, which are fabricated from a thin perforated or apertured sheet of metal, preferably nickel. In a similar manner as the cathode current collector 40, the anode current collectors 42, 44 are apertured screen-type members to which the anode active material, preferably lithium, is contacted. Upon pressing, lithium, being a relatively soft metal, moves into the apertures in the current collectors 42, 44 to "lock" the anode plates 36 and 38 to the current collectors. However, since the anode plates 36 and 38 only face a respective sidewall 34A and 34B of the cathode plate 34, there is no need to contact anode active material to the opposite sides of the current collectors 42, 44. Instead, the bare sides of the anode current collectors 42 and 44 contact the respective casing container sidewalls 18 and 20 to help make electrical connection to the casing.

Further, the anode current collectors 42 and 44 each have a tab 42A and 44A that extends outwardly beyond a respective upper edge 36A and 38A of the anode plates 36 and 38. The outwardly extending anode current collector tabs 42A and 44A are electrically connected to an inner surface of the sidewalls 18 and 20 by respective welds 46 and 48. Thus, the cathode 34 electrically connected to the terminal pin 30 serves as the positive terminal for the electrochemical cell 10 and the anode plates 36, 38 flanking the cathode 34 are electrically connected to the casing 12 serving as the negative terminal for the cell. This construction means that the electrochemical cell 10 has a case-negative design. Such a cell construction is shown in U.S. Pat. No. 5,250,373 to Muffoletto et al., which is assigned to the assignee of the present invention and incorporated herein by reference.

As shown in FIGS. 2 and 3, the cathode 34 is enclosed in a primary separator 50 that, except for an opening 50A, substantially surrounds and envelopes the cathode 34. The cathode connector tab 40B extends outwardly through the opening 50A in the primary separator 50 to electrically connect to the proximal portion 30A of the terminal pin 30. The primary separator 50 in turn is housed in a free-standing secondary separator 52. Whereas except for the opening 50A, the primary separator 50 is a closed envelope surrounding the cathode 34, the free-standing secondary separator 52 is an open-ended bag-shaped structure comprising spaced apart front and back separator sidewalls 52A and 52B joined by a curved end wall 52C. The curved separator end wall 52C meeting the separator sidewalls 52A and 52B all extend upwardly to form an open-ended annular edge 52D. The annular edge 52D of the secondary separator 52 is spaced a relatively short distance "x" ranging from about 0.0 inches (contacting the inner surface 16A of the lid 16) to about 0.05 inches from the inner surface of the lid 16.

An important aspect of the secondary separator 52 is that it resides between the anode tabs 42A and 44A welded to the inner surface of the open-ended casing container 14 and the proximal portion 30A of the terminal pin 30 extending downwardly into the casing 12 from the glass-to-metal seal 32 to electrically connect to the cathode current collector tab 40B. That way, with the cathode 34 enveloped in the primary separator 50, the free-standing secondary separator bag 52 provides an added layer of separator material between the opposite polarity electrodes. The demand to make electrochemical cells smaller and smaller to power ever increasingly smaller devices, for example, medical devices that are intended to long-term implantation in the human body, means that the distance between opposite polarity components in such cells is becoming shorter and shorter. Thus, there is a desire to not only provide two layers of separator material as redundant structures keeping the opposite polarity electrode active materials (anode and cathode active materials) from direct physical contact with each other, but there must also be a physical barrier keeping non-active terminal structures such as leads and terminal pins from contacting each other. The primary separator 50 prevents the anode plates 36 and 38 from physically contacting the intermediate cathode 34. The secondary separator 52 not only provides a degree of redundancy keeping the anode plates 36 and 38 from physically contacting the intermediate cathode 34, but it also provides a physical barrier keeping the anode current collector tabs 42A and 44A from contacting the cathode current collector tab 408 electrically connected to the proximal portion 30A of the terminal pin 30.

In that respect, the primary and secondary separators 50 and 52 are each of an electrically insulative material that is both chemically unreactive with the anode and cathode active materials and chemically unreactive with and insoluble in the electrolyte. In addition, the primary and secondary separators 50 and 52 have a degree of porosity that allows flow there through of the electrolyte during electrochemical reactions of the cell 10. Illustrative separator materials include fabrics woven from fluoropolymeric fibers including polyvinylidine fluoride, polyethylenetetrafluoroethylene, and polyethylenechlorotrifluoroethylene used either alone or laminated with a fluoropolymeric macroporous film, non-woven glass, polypropylene, polyethylene, glass fiber materials, ceramics, polytetrafluoroethylene membrane commercially available under the designation ZITEX (Chemplast Inc.), polypropylene/polyethylene membrane commercially available under the designation CELGARD (Celanese Plastic Company, Inc.), a membrane commercially available under the designation DEXIGLAS (C. H. Dexter, Div., Dexter Corp.), and a polyethylene membrane commercially available from Tonen Chemical Corp.

The exemplary electrochemical cell 10 of the present invention further includes a nonaqueous, ionically conductive electrolyte that serves as a medium for migration of ions between the anode plates 36, 38 and the cathode 34 during electrochemical reactions of the cell. The electrochemical reactions at the electrodes involves conversion of ions in atomic or molecular forms that migrate from the anode plates 36, 38 to the cathode 34. Thus, nonaqueous electrolytes suitable for the present electrochemical cell 10 are substantially inert to the anode and cathode active materials, and they exhibit those physical properties necessary for ionic transport, namely, low viscosity, low surface tension and wettability.

A suitable electrolyte has an inorganic, ionically conductive salt dissolved in a mixture of aprotic organic solvents comprising a low viscosity solvent and a high permittivity solvent. In the case of the anode plates 36, 38 comprising lithium, preferred lithium salts that are useful as a vehicle for transport of alkali metal ions from the anode plates to the cathode 34 include $LiPF_6$, $LiBF_4$, $LiAsF_5$, $LiSbF_6$, $LiClO_4$, $LiO_2$, $LiAlCl_4$, $LiGaCl_4$, $LiC(SO_2CF_3)_3$, $LIN(SO_2CF_3)_2$, $LiSCN$, $LiO_3SCF_3$, $LiC_6F_5SO_3$, $LiO_2CCF_3$, $LiSO_6F$, $LiB(C_6H_5)_4$, $LiCF_3SO_3$, and mixtures thereof.

Low viscosity solvents useful with the exemplary electrochemical cell 10 include esters, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy, 2 methoxyethane (EME), ethyl methyl carbonate, methyl propyl carbonate, ethyl propyl carbonate, diethyl carbonate, dipropyl carbonate, and mixtures thereof, and high permittivity solvents include cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GEL), N-methyl-2-pyrrolidone (NMP), and mixtures thereof. In the exemplary electrochemical cell 10 of a primary chemistry, the preferred anode is lithium metal, the preferred cathode active material is SVO or $CF_x$, or a combination of SVO and $CF_x$ (see U.S. Pat. No. 6,551,747 to Gan, which is assigned to the assignee of the present invention and incorporated herein by reference) and the preferred electrolyte is 0.8M to 1.5M $LiAsF_6$ or $LiPF_6$ dissolved in a 50:50 mixture, by volume, of propylene carbonate and 1,2-dimethoxyethane.

The corrosion resistant glass used in the glass-to-metal seal 32 has up to about 50% by weight silicon such as CABAL 12, TA 23, FUSITE 425 or FUSITE 435. The positive terminal pin 30 preferably comprise molybdenum, although titanium, aluminum, nickel alloy, or stainless steel can also be used. The open-ended container 14 of the cell casing 12 is of a conductive material selected from nickel, aluminum, stainless steel, mild steel, tantalum and titanium. The lid 16 hermetically sealed to the open-end of the container 14 is of a conductive material that is similar to that of the container 14.

By way of example, in the illustrative exemplary electrochemical cell 10 of the present invention, the anode plates 36 and 38 comprise lithium contacted to nickel current collectors 42 and 44. The cathode active material comprising the cathode plate 34 is preferably comprised of a metal, a metal oxide, a mixed metal oxide, a metal sulfide, a carbonaceous material, or a fluorinated carbon material, and the cathode current collector 36 is fabricated from a relatively thin sheet of metal selected from the group of nickel, aluminum, stainless steel, mild steel and titanium, with titanium being preferred.

In the case of a carbonaceous cathode active material, the carbonaceous material preferably is prepared from carbon and fluorine, and includes graphitic and non-graphitic forms of carbon, such as coke, charcoal or activated carbon. The fluorinated carbon is represented by the formula $(CF_x)_n$, wherein x varies between about 0.1 to 0.9 and preferably between 0.5 and 1.2, and $(C_2F)_n$, wherein the "n" refers to the number of monomer units, which can vary widely. The preferred cathode active mixture comprises $CF_x$ combined with at least one of a number of discharge promoter components such as acetylene black, carbon black and graphite. Metallic powders such as nickel, aluminum, titanium, and stainless steel in powder form are also useful as conductive diluents when mixed with the cathode active mixture of the present invention. If required, a binder material can also be used. Preferred binders comprise fluoro-resins in powdered form such as powdered polytetrafluoroethylene (PTFE).

Exemplary mixed metal oxide materials include silver vanadium oxide (SVO) as described in U.S. Pat. Nos. 4,310,609 and 4,391,729 to Liang et al., or copper silver vanadium oxide (CSVO) as described in U.S. Pat. Nos. 5,472,810 and 5,516,340 to Takeuchi et al., all assigned to the assignee of the present invention, the disclosures of which are hereby incorporated by reference. The SVO and CSVO materials are also preferably mixed with a discharge promoter component and a binder material. In the case of the cathode comprised of a carbonaceous active material, the preferred electrolyte is 1.0 M to 1.4 M $LiBF_4$ in γ-butyrolactone. A cell having a metal-containing cathode active material is preferably activated with an electrolyte of 1.0 M to 1.4 M $LiAsF_6$ or $LiPF_6$ in a 50:50 mixture of, by volume, 1,2-dimethoxyethane and propylene carbonate. The terminal pin 30 is of molybdenum, titanium, or aluminum.

The electrochemical cell of the present invention can also be constructed having a case-positive electrical configuration by electrically connecting the cathode 34 to the conductive cell casing 12 and with the anode plates 36, 38 being electrically connected to the terminal pin 30.

Furthermore, the present separator assembly is readily incorporated into secondary electrochemical systems. Exemplary secondary cells include carbonaceous anode plates 36, 38 and a lithium-retentive cathode 34, such as $LiCoO_2$, activated with an electrolyte having 0.8 to 1.5 molar $LiAsF_6$ or $LiPF_6$ dissolved in an equilibrated mixture of dimethyl carbonate, ethyl methyl carbonate, diethyl carbonate and ethylene carbonate. Such a secondary chemistry is more thoroughly described in U.S. patent application Ser. No. 09/669,936, filed Sep. 26, 2000, now abandoned, which application is assigned to the assignee of the present invention and incorporated by reference herein.

While the exemplary electrochemical cell 10 has been described in connection with certain preferred embodiments, that is not intended to limit the scope of the present invention to the particular forms set forth, but, on the contrary, the present invention is intended to cover such alternatives, modifications, and equivalents as may be included within the scope of the appended claims.

What is claimed is:

1. An electrochemical cell, comprising :
   a) a casing comprising an open-ended container closed by a lid;
   b) a first electrode housed inside the casing, the first electrode being electrically connected to a first terminal for the electrochemical cell;

c) a second, counter electrode housed inside the casing, the second electrode being electrically connected to a second terminal for the electrochemical cell;

d) a primary separator enveloping the first electrode;

e) a secondary separator comprising an open-ended bag-shaped member extending to an open annular edge, wherein the primary separator enveloping the first electrode is contained in the secondary separator; and f) an electrolyte provided in the casing to activate the first and second electrodes.

2. The electrochemical cell of claim 1, wherein the secondary separator is a free-standing open-ended bag-shaped member.

3. The electrochemical cell of claim 1, wherein the lid has an inner surface, and wherein the open annular edge of the secondary separator is in a relatively closely spaced relationship with the inner surface of the lid.

4. The electrochemical cell of claim 3, wherein the relatively closely spaced relationship of the open annular edge of the secondary separator with respect to the inner surface of the lid ranges from about 0.0 inches to about 0.05 inches.

5. The electrochemical cell of claim 1, wherein the lid supports a terminal pin electrically isolated from the casing by a glass-to-metal seal, the first electrode being electrically connected to the terminal pin serving as the first terminal for the electrochemical cell, and wherein the second electrode is electrically connected to the casing serving as the second terminal for the electrochemical cell, and wherein the open annular edge of the secondary separator resides between the first electrode connected to the terminal pin and the second electrode connected to the casing.

6. The electrochemical cell of claim 5, wherein the first electrode comprises a first electrode active material contacted to a first electrode current collector having an outwardly extending first electrode current collector tab electrically connected to the terminal pin, and wherein the second electrode comprises a second electrode active material contacted to at least one second electrode current collector having an outwardly extending second electrode current collector tab electrically connected to an inner surface of the casing, and wherein the open annular edge of the secondary separator resides between the first electrode current collector tab electrically connected to the terminal pin and the second electrode current collector tab electrically connected to the casing.

7. The electrochemical cell of claim 1, wherein the lid supports a terminal pin electrically isolated from the casing by a glass-to-metal seal, and wherein the first electrode has spaced-apart major sides extending to an intermediate edge, the first electrode comprising a first electrode active material contacted to a first electrode current collector having a first electrode current collector tab extending outwardly from the intermediate edge and being electrically connected to the terminal pin serving as the first terminal for the electrochemical cell, and wherein the second electrode comprises at least two second electrode plates flanking respective ones of the spaced-apart major sides of the first electrode, the second electrode plates each comprising a second electrode active material contacted to a second electrode current collector having an outwardly extending second electrode current collector tab electrically connected to an inner surface of the casing serving as the second terminal for the electrochemical cell, and wherein the open annular edge of the secondary separator resides between the first current collector tab electrically connected to the terminal pin and the at least two second electrode current collector tabs electrically connected to the inner surface of the casing.

8. The electrochemical cell of claim 1, wherein the first electrode is a cathode and the second electrode is an anode.

9. The electrochemical cell of claim 8, wherein the cathode has spaced apart major sides extending to an intermediate radiused curved edge, and wherein the anode flanks the cathode adjacent to its major sides.

10. The electrochemical cell of claim 1, wherein the container of the casing comprises spaced-apart container sidewalls joined by an intermediate container end wall having a radius curved shape, and wherein the secondary separator comprises spaced apart secondary separator sidewalls joined by an intermediate secondary separator end wall having a radius curved shape, the shape of the spaced apart secondary separator sidewalls and the intermediate secondary separator end wall generally matching the shape of the spaced-apart container sidewalls and the intermediate container end wall.

11. The electrochemical cell of claim 1, of either a Li/silver vanadium oxide (SVO) chemistry or a lithium/$CF_x$ chemistry.

12. The electrochemical cell of claim 1, of a carbonaceous anode material/lithium-retentive cathode active material.

13. An electrochemical cell, comprising :

a) a casing comprising an open-ended container closed by a lid;

b) a terminal pin supported by the lid and being electrically isolated from the casing by a glass-to-metal seal;

c) a cathode housed inside the casing, the cathode comprising a cathode active material contacted to a cathode current collector having an outwardly extending cathode current collector tab electrically connected to the terminal pin serving as a positive terminal for the electrochemical cell;

d) a primary separator enveloping the cathode;

e) an anode housed inside the casing, the anode comprising an anode active material contacted to at least one anode current collector having an outwardly extending anode current collector tab electrically connected to an inner surface of the casing serving as a negative terminal for the electrochemical cell;

f) a secondary separator comprising an open-ended bag-shaped member extending to an open annular edge, wherein the primary separator enveloping the cathode is contained in the secondary separator, and wherein the open annular edge of the secondary separator resides between the cathode current collector tab electrically connected to the terminal pin and the anode current collector tab electrically connected to the casing; and g) an electrolyte provided in the casing to activate the anode and the cathode.

14. The electrochemical cell of claim 13, wherein the cathode has spaced-apart major sides extending to an intermediate edge, the cathode comprising a cathode active material contacted to a cathode current collector having a cathode current collector tab extending outwardly from the intermediate edge and being electrically connected to the terminal pin serving as the positive terminal for the electrochemical cell, and wherein the anode comprises at least two anode plates flanking respective ones of the spaced-apart major sides of the cathode, the anode plates each comprising an anode active material contacted to an anode current collector having an outwardly extending anode current collector tab electrically connected to an inner surface of the casing serving as the negative terminal for the electrochemical cell, and wherein the open annular edge of the secondary separator resides between the cathode current collector tab electrically connected to the terminal pin and the at least two anode current collector tabs electrically connected to the inner surface of the casing.

15. A method for providing an electrochemical cell, comprising the steps of:
   a) providing a container having a container side wall extending to an edge surrounding a container opening;
   b) housing a first electrode inside a primary separator envelope and then electrically connecting the first electrode to a first terminal for the electrochemical cell;
   c) providing a secondary separator comprising an open-ended bag-shaped member extending to an open annular edge;
   d) positioning the first electrode housed inside the primary separator envelope inside the secondary separator;
   e) positioning a second, counter electrode housed inside the casing and then electrically connecting the second electrode to a second terminal for the electrochemical cell;
   f) positioning the secondary separator so that its open annular edge resides between the first electrode electrically connected to the first terminal for the electrochemical cell and the second electrode electrically connecting the second terminal for the electrochemical cell; and
   g) activating the first and second electrodes with an electrolyte provided in the casing.

16. The method of claim 15, including providing the secondary separator as a free-standing open-ended bag-shaped member.

17. The method of claim 15, including providing the lid having an inner surface with the open annular edge of the secondary separator being in a relatively closely spaced relationship with the inner surface of the lid.

18. The method of claim 17, including providing the relatively closely spaced relationship of the open annular edge of the secondary separator with respect to the inner surface of the lid ranging from about 0.0 inches to about 0.05 inches.

19. The method of claim 15, including providing:
   a) the lid supporting a terminal pin electrically isolated from the casing by a glass-to-metal seal
   b) electrically connecting the first electrode to the terminal pin serving as the first terminal for the electrochemical cell;
   c) electrically connecting the second electrode to the casing serving as the second terminal for the electrochemical cell; and
   d) positioning the open annular edge of the secondary separator between the first electrode electrically connected to the terminal pin and the second electrode electrically connected to the casing.

20. The method of claim 19, including providing:
   a) the first electrode comprising a first electrode active material contacted to a first electrode current collector having an outwardly extending first electrode current collector tab, and electrically connecting the first electrode current collector tab to the terminal pin;
   b) the second electrode comprising a second electrode active material contacted to at least one second electrode current collector having an outwardly extending second electrode current collector tab, and electrically connecting the second electrode current collector tab an inner surface of the casing; an
   c) positioning the open annular edge of the secondary separator between the first electrode current collector tab electrically connected to the terminal pin and the second electrode current collector tab electrically connected to the casing.

21. The method of claim 15, including providing:
   a) the lid supporting a terminal pin electrically isolated from the casing by a glass-to-metal seal;
   b) providing the first electrode having spaced-apart major sides extending to an intermediate edge, the first electrode comprising a first electrode active material contacted to a first electrode current collector having a first electrode current collector tab extending outwardly from the intermediate edge, and electrically connecting the first electrode current collector tab to the terminal pin serving as the first terminal for the electrochemical cell;
   c) providing the second electrode comprising at least two second electrode plates flanking respective ones of the spaced-apart major sides of the first electrode, the second electrode plates each comprising a second electrode active material contacted to a second electrode current collector having an outwardly extending second electrode current collector tab, and electrically connecting each of the at least two second electrode current collector tabs to an inner surface of the casing serving as the second terminal for the electrochemical cell; and
   d) positioning the open annular edge of the secondary separator between the first current collector tab electrically connected to the terminal pin and the at least two second electrode current collector tabs electrically connected to the inner surface of the casing.

\* \* \* \* \*